(12) United States Patent
Schulze et al.

(10) Patent No.: US 10,650,127 B2
(45) Date of Patent: *May 12, 2020

(54) MANAGING PERMISSIONS

(71) Applicant: Lifetrack Medical Systems Private Ltd., Singapore (SG)

(72) Inventors: Eric Schulze, Global (PH); Brendan Philip Rees, Global (PH)

(73) Assignee: LIFETRACK MEDICAL SYSTEMS PRIVATE LTD., Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 16/392,331

(22) Filed: Apr. 23, 2019

(65) Prior Publication Data
US 2019/0311091 A1 Oct. 10, 2019

Related U.S. Application Data

(63) Continuation of application No. 15/635,089, filed on Jun. 27, 2017, now Pat. No. 10,339,286, which is a continuation of application No. 15/209,486, filed on Jul. 13, 2016, now Pat. No. 9,705,931.

(51) Int. Cl.
| | | |
|---|---|---|
| *G06F 21/00* | (2013.01) | |
| *G06F 21/31* | (2013.01) | |
| *G06F 21/60* | (2013.01) | |
| *G06Q 50/22* | (2018.01) | |
| *H04L 29/06* | (2006.01) | |
| *G06F 21/45* | (2013.01) | |

(52) U.S. Cl.
CPC ........... *G06F 21/31* (2013.01); *G06F 21/45* (2013.01); *G06F 21/604* (2013.01); *G06Q 50/22* (2013.01); *H04L 63/10* (2013.01); *H04L 63/102* (2013.01); *H04L 63/105* (2013.01); *H04L 63/20* (2013.01); *G06F 2221/2141* (2013.01); *G06F 2221/2145* (2013.01); *H04L 63/104* (2013.01)

(58) Field of Classification Search
CPC ............ G06F 16/9024; G06F 19/3418; G06F 21/604; G06F 21/6218; G06F 2221/2141
See application file for complete search history.

(56) References Cited

U.S. PATENT DOCUMENTS

| | | | |
|---|---|---|---|
| 6,460,141 B1 | 10/2002 | Olden | |
| 9,276,958 B2* | 3/2016 | Hagiwara | ............... H04L 63/20 |
| 9,705,931 B1 | 7/2017 | Schulze et al. | |

(Continued)

FOREIGN PATENT DOCUMENTS

| | | |
|---|---|---|
| WO | WO 2015/095597 | 6/2015 |
| WO | WO 2018/011717 | 1/2018 |

OTHER PUBLICATIONS

U.S. Appl. No. 15/635,089, filed Jun. 27, 2017—Allowed 20180018448, Jan. 18, 2018.

(Continued)

*Primary Examiner* — Ghazal B Shehni
(74) *Attorney, Agent, or Firm* — Fish & Richardson P.C.

(57) ABSTRACT

In general, an indication is received through a user interface of an intention of a potential rider to use an autonomous vehicle. In response to the receipt of the indication, a hailing request is sent by a signaling mode to at least one autonomous vehicle that can receive the hailing request directly in accordance with the signaling mode.

26 Claims, 19 Drawing Sheets

(56) References Cited

U.S. PATENT DOCUMENTS

Figure 1:
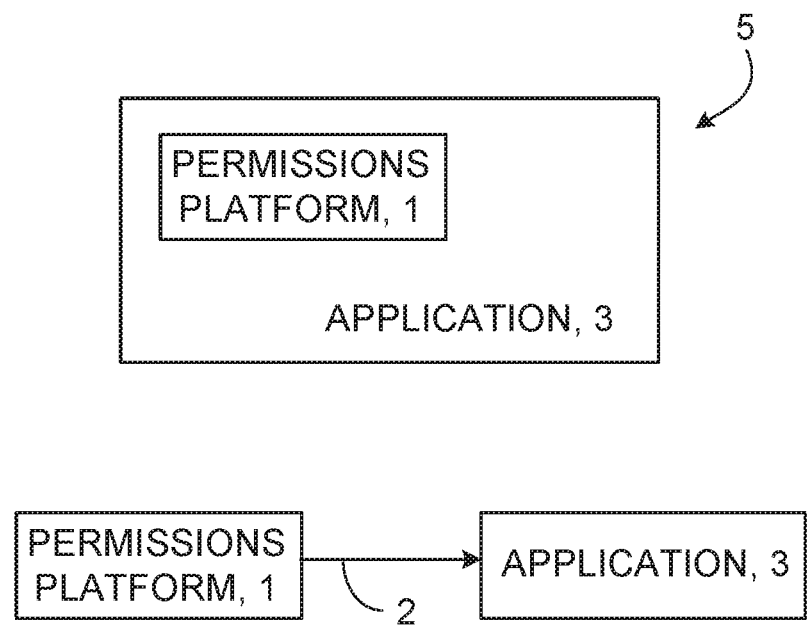

| | | | |
|---|---|---|---|
| 2002/0157023 A1* | 10/2002 | Callahan | H04L 63/0227 726/4 |
| 2004/0004632 A1 | 1/2004 | Knight et al. | |
| 2005/0075544 A1 | 4/2005 | Shapiro | |
| 2009/0300544 A1 | 12/2009 | Psenka | |
| 2010/0070897 A1 | 3/2010 | Aymeloglu | |
| 2011/0213634 A1 | 9/2011 | Karakey | |
| 2011/0277017 A1 | 11/2011 | Ivanov et al. | |
| 2012/0290920 A1 | 11/2012 | Crossley | |
| 2014/0215604 A1 | 7/2014 | Giblin | |
| 2015/0320365 A1 | 11/2015 | Schulze et al. | |
| 2015/0324075 A1 | 11/2015 | Schulze et al. | |
| 2016/0124581 A1 | 5/2016 | Schulze et al. | |
| 2016/0328577 A1 | 11/2016 | Howley | |
| 2018/0018448 A1 | 1/2018 | Schulze et al. | |
| 2019/0138161 A1 | 5/2019 | Schulze et al. | |

OTHER PUBLICATIONS

U.S. Appl. No. 15/804,131, filed Nov. 6, 2017—Pending.

Dolgobrod, Maxim, "Developing a user interface for a cross-platform web application", Helsinki Metropolia University of Applied Sciences, Master's Thesis, Information Technology, May 30, 2013 (99 pages).

EP Extended European Search Report in European application 17827092.2, dated Apr. 10, 2019, 8 pages.

International Preliminary Report on Patentability from PCT application PCT/IB2017/054184 dated Jan. 24, 2019 (8 pages).

International Search Report and Written Opinion issued in PCT application PCT/US2018/059392 dated Jan. 29, 2019 (19 pages).

Application as filed and pending claims from U.S. Appl. No. 15/804,131, filed Nov. 6, 2017.

PCT International Search Report and Written Opinion from PCT applicaton PCT/US2018/059392, dated Jan. 29, 2019, 15 pages.

Samarati et al., "Access control: Policies, Models, and Mechanisms," Foundations of Security Analysis and Design: Tutorial Lectures, Sep. 2000, 2171: 137-196.

Sandhu et al., "Access control: principle and practice," IEEE Communications Magazine, Sep. 1994, 32(9): 40-48.

USPTO Transaction History for U.S. Appl. No. 15/209,486, filed Jul. 13, 2016, 140 pages.

USPTO Transaction History for U.S. Appl. No. 15/635,089, filed Jun. 27, 2017, 296 pages.

U.S. Appl. No. 15/804,131, filed Nov. 6, 2017 (includes claims as of Oct. 18, 2018), 26 pages.

Australian Examination Report for Australian Application No. 2017296139, dated Sep. 10, 2019, 7 pages.

U.S. Appl. No. 15/209,486, filed Jul. 13, 2016—Issued U.S. Pat. No. 9,705,931, Jul. 11, 2017.

U.S. Appl. No. 15/635,089, filed Jun. 27, 2017—Issued U.S. Pat. No. 10,339,286, Jul. 2, 2019.

U.S. Appl. No. 16/392,331, filed Apr. 23, 2019—Pending.

U.S. Appl. No. 15/804,131, filed Nov. 6, 2017—Published 20190138161.

* cited by examiner

HTTPS://N2.LIFETRACKMEDICALSYSTEMS.COM/RIS/USERMANAGEMENT/INDEX.PHP

LIFETRACK MEDICAL SYSTEMS

[ ADD NEW USER ] [ LIST USERS ]
[ DELETE SELECTED USER ]
[ FINISHED CUSTOMIZING FAF ]

AVAILABLE FIELDS AND FEATURES
ACTIVE TEMPLATE ATTRIBUTES [ATTRIBUTE]

| FIELD OR FEATURE | INTERFACE NAME | TOOL TIP | IN SCOPE |
|---|---|---|---|
| ACTV12 | TDD9 | | ADD |
| ACTV13 | ICTST | | ADD |
| ACTV15 | ICD | | ADD |
| ACTV17 | PPT | | ADD |
| ACTV20 | CPT | | ADD |

CUSTOM FIELDS [CUSTOMFIELD]

| FIELD OR FEATURE | INTERFACE NAME | TOOL TIP | IN SCOPE |
|---|---|---|---|
| CUSTOM_001 | QA STATUS | | ADD |
| CUSTOM_002 | FAX REQUEST | | REMOVE |
| CUSTOM_003 | UPLOAD DOCUMENT IMAGES | | ADD |
| CUSTOM_005 | DISCREPANCY | | REMOVE |
| CUSTOM_006 | TF CASES | | ADD |
| CUSTOM_007 | INT DISCREPANCY | | ADD |
| CUSTOM_008 | ONSITE REPORT | | REMOVE |
| CUSTOM_009 | ADDENDUM | | ADD |
| CUSTOM_010 | COMP/TEST | | ADD |
| CUSTOM_011 | DISCREPANCY DETAILS | | REMOVE |

AVAILABLE FIELDS AND FEATURES
CUSTOM FIELDS [CUSTOMFIELD]

| FIELD OR FEATURE | INTERFACE NAME | TOOL TIP | IN SCOPE |
|---|---|---|---|
| CUSTOM_002 | FAX REQUEST | | REMOVE |
| CUSTOM_005 | DISCREPANCY | | REMOVE |
| CUSTOM_008 | ONSITE REPORT | | REMOVE |
| CUSTOM_011 | DISCREPANCY DETAILS | | REMOVE |
| CUSTOM_021 | CHRIS | | REMOVE |
| CUSTOM_024 | PRELIM RAD | | REMOVE |

FIG. 8

| | | |
|---|---|---|
| CUSTOM_014 | BIZBOX | ADD |
| CUSTOM_018 | CALL REPORT | ADD |
| CUSTOM_019 | ABR | ADD |
| CUSTOM_020 | COMMUNICATIONS | ADD |
| CUSTOM_021 | CHRIS | REMOVE |
| CUSTOM_022 | DATE ASSIGNED TO RADS | ADD |
| CUSTOM_023 | INITIAL RAD | ADD |
| CUSTOM_024 | PRELIM RAD | REMOVE |
| CUSTOM_025 | QA TEAM | ADD |
| CUSTOM_026 | DEMO | ADD |
| CUSTOM_027 | DEMO | ADD |
| CUSTOM_028 | DEMO TEST | ADD |
| CUSTOM_029 | TF CASES | ADD |

LIFETRACK
MEDICAL SYSTEMS
VERSION 2.0.104

NAME: DAVID
USER ID: DAVID
ACCOUNT TYPE: ORIGIN
FAV SCOPE: DAVID

[ADD FIELDS AND FEATURES] [CREATE NEW FAV TEMPLATE]

SELECT TEMPLATE: [ ▼ ]
SELECT USER: [AG23SKIDOO ▼] — 311

CUSTOM FIELDS [CUSTOMFIELD]

| FIELD OR FEATURE | INTERFACE NAME | TOOL TIP | |
|---|---|---|---|
| CUSTOM_002 | FAX REQUEST | | REMOVE |
| CUSTOM_005 | DISCREPANCY | | REMOVE |
| CUSTOM_008 | ONSITE REPORT | | REMOVE |
| CUSTOM_011 | DISCREPANCY DETAILS | | REMOVE |
| CUSTOM_021 | CHRIS | | REMOVE |
| CUSTOM_024 | PRELIM RAD | | |

[SAVE FAF SCOPE]

PLEASE NOTE: CHANGES ARE NOT STORED ON THE SERVER UNTIL THEY ARE SAVED

FIG. 20 (Cont.)

MANAGING PERMISSIONS

CROSS-REFERENCE TO RELATED APPLICATIONS

This application is a continuation application of and claims priority to U.S. application Ser. No. 15/635,089, filed on Jun. 27, 2017, and U.S. application Ser. No. 15/209,486, filed on Jul. 13, 2016, the contents and disclosures of both of which are incorporated herein by reference in their entirety.

This description relates to U.S. patent application Ser. No. 14/279,782, filed May 16, 2014 and Ser. No. 14/272,021, filed May 7, 2014, both of which are incorporated here by reference in their entireties.

BACKGROUND

This description relates to managing permissions.

Permissions can be used, for example, to define which features of an application can be accessed and used by which users of the application.

For a large enterprise, the number and variety of features offered by an application can be quite large. Features of an application sometimes support complex flows of work being done by various users in an enterprise. The complex flows may correspond to roles that the users play (e.g., jobs that they have) within the enterprise. In some cases, it is desirable or even critical that users have access only to those features that they need in order to perform their roles.

A given feature can be subject to different kinds of access by users. Some users may have access only to know that the feature exists, for example, by observing a grayed control representing the feature in a user interface, without being able to invoke the feature. Some users may not see the features at all. Some users may have access to invoke and use the feature, for example, by clicking on a button in a user interface.

An enterprise often controls which users of an application can have access (e.g., through a user interface) to which features. Access can be controlled based on the roles of the users, for example, within a hierarchical structure of the enterprise. The hierarchy may be important in that, for example, all of the customer service representatives of an enterprise may have the same permissions, and those permissions may be fewer than the permissions of the manager to whom they report, and so on. We sometimes say that the enterprise, by controlling access, is managing permissions in that permissions are given or withheld for various users to have access to features.

As people are hired, promoted, or depart from an enterprise, as roles change, and as features of an application are changed, permissions need to be updated. For a large enterprise, changes will occur daily or even many times a day. For that reason, typically developers design an application to include a limited set of "hard-wired" functions that enable administrators of the enterprise to manage certain aspects of permissions for the application, rather than requiring the changes to be made by a developer.

A common model for such permissions management functions is a role-permissions model in which specific users are assigned specific roles to each of which a limited number of permissions have been assigned that support the role that the user plays in the enterprise. The role-permissions model implies a matrix in which, for example, the roles appear in successive rows and the assignable features that users in various roles can be granted permission to access appear in respective columns.

Typically, the administrator is given the authority to create, modify, or change profile information about authorized users of the application; to assign or reassign each user to one of the roles for which a given subset of the assignable features have been assigned based on the operating structure of the enterprise; and in some cases to change the features for which all users in a given role have permission. To properly program the permissions management functions of the application, the developer of the application needs to have a working knowledge of each role that users of the enterprise may play, the typical workflow of each role in the enterprise; and the features of the application the permissions to which may need to be restricted based on the workflow and business requirements of the enterprise. Because of the expense and effort of developing administrator functions in an application, only a limited set of such functions can be provided. When the number of roles and the number of features are large, the developer normally must constrain the number of features that can be selectively associated with each role. As a result, the administrator may be constrained to managing a relatively small number of different roles of users of the enterprise and a relatively small number of features for which permissions can be assigned to roles.

For example, for a radiology department of a large medical facility, the developer of an application may be able to include a predefined set of only about 10 to 20 roles and only about 10 to 20 features that can be assigned to each role, yielding a 20 by 20 permission matrix. On one hand, the matrix can be cumbersome to use because a viewer must view 400 potential cells in the matrix to understand which roles have which permissions. On the other hand, the limited numbers of roles and features represented by the 400 cells can severely limit the flexibility of the permissions management task.

SUMMARY

These and other aspects, features, implementations, and advantages, and combinations of them, can be expressed as methods, systems, components, apparatus, program products, methods of doing business, means and steps for performing functions, and in other ways.

Other aspects, features, implementations, and advantages will become apparent from the following description and from the claims.

DESCRIPTION

Figure 2:
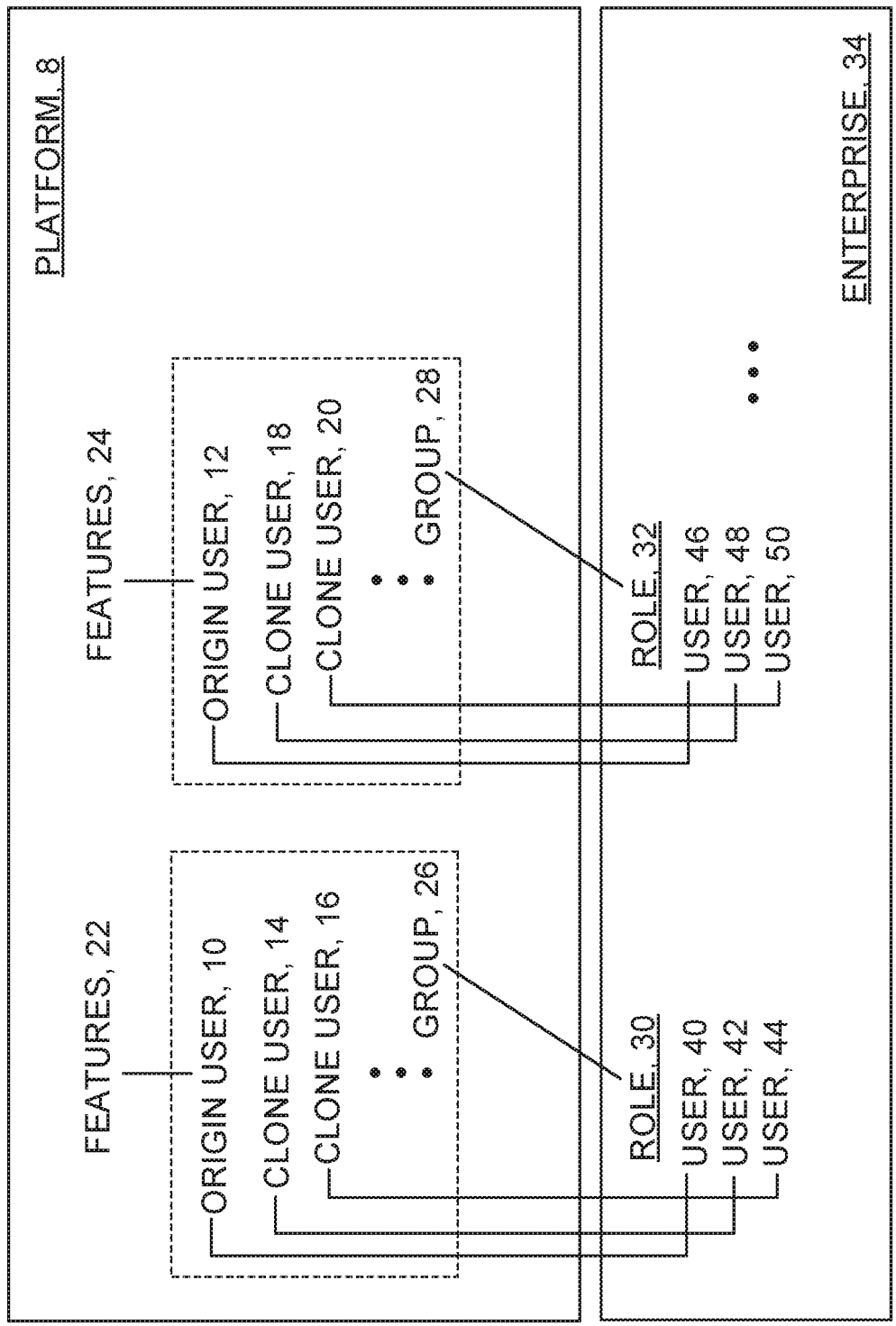
Figure 3:
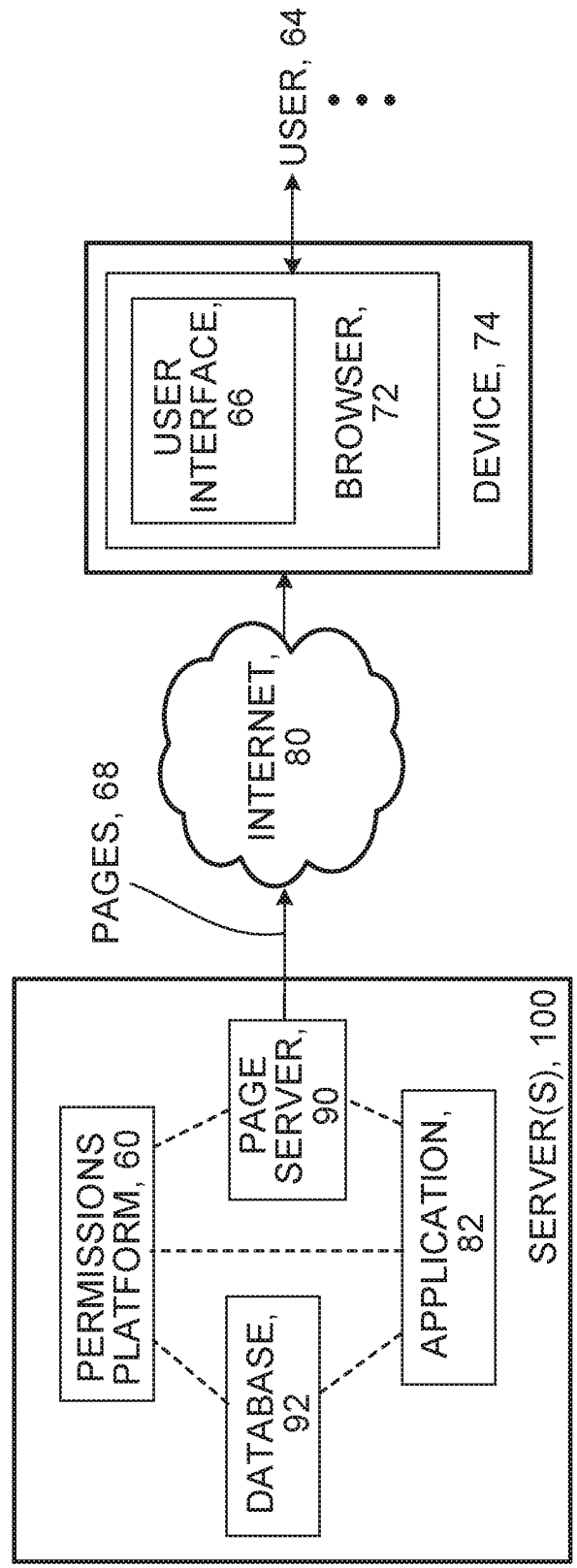

FIGS. 1 through 3 are block diagrams.
FIGS. 4 through 21 are screen shots.

In some implementations of the systems and techniques that we describe here (which we sometimes refer to as a "permissions platform"), permissions can be managed effectively, quickly, and efficiently, and at a fine-grained level. Essentially no constraints are imposed on the management of the permissions with respect to the roles of users or the number of the roles, the number of users, or the number, type, or complexity of the combinations of features for which permissions are to be managed for users or roles. Development of these flexible permissions functions for applications is itself made extremely simple and quick. Developers need not have a detailed understanding of the roles of an enterprise, the workflows followed by users in those roles, or the selections of features that may need to be associated with each of the roles or with individual users. Instead, the administrators can easily and quickly add, update, or remove users; associate an essentially unlimited number of different roles in the enterprise with respective groups of users in the permissions platform; and assign any one or more selected features to any of the groups (and therefore implicitly to the corresponding roles in the enterprise).

As shown in FIG. 1, the permissions platform 1 can be operated separately from [2] or be incorporated [5] easily and simply into any application 3 being developed or already in existence, because doing so requires only the identification by or on behalf of, for example, the developer (or perhaps automatically) of every feature (or every feature of interest) of the application to which a user may need to have access. Details about the features of an example of such an application are contained in the two patent applications referred to above. Once the features have been identified, the administrator easily can populate the permissions platform with users, associate users with roles, and assign any arbitrary set of features to each of the users or roles, without requiring involvement of a developer.

Thus among the important aspects of the permissions platform are that constraints of the kind implied by the role-permission model are eliminated. Every feature of an application (and in particular every feature that can be exposed and accessible through a user interface such as a web browser) can be independently assignable to any user of the application. The result is that the developer of any application that uses the permissions platform need have essentially no understanding of the enterprise workflows and no understanding of the enterprise roles, because each user can be assigned an entirely unique set of the features easy and simply by the administrator. The permissions platform can easily implement highly granular and finely tuned permissions structures, for example, permission structures related to any workflow of an enterprise.

Although it would be possible in the permissions platform to require an administrator to specify the exact set of features that will be permitted for each individual user, such a configuration may be impractical and onerous, especially when the number of users is large. A copy function could be provided to enable the administrator to copy a set of permitted features of a user to another user, for example if they both had the same role in the enterprise, but if changes were needed for permitted features for users of that role the copying process would have to be repeated.

To deal with this concern, the permissions platform provides another important function that enables an administrator (or any other user who has permission to use the feature) to group users. Permissions within a group are inherited in that the permitted feature set of one user (called the origin user) defines the permitted feature set of the all of the users (including clone users) of the group enabling the administrator to easily administer the permissions (and hence roles) of a group of users in a way that is flexible and powerful.

As shown in FIG. 2, this grouping function is accomplished in some implementations of the permissions platform 8 by first requiring that every user be designated either as an "origin user" 10, 12 or a "clone user" 14, 16, 18, 20. The designation of a user within one or the other of the categories can be made when the user is first included in the permissions platform and can be changed at any time by any user who has the permission to use that category designation feature.

In general, origin users and clone users have the same kinds of characteristics within the permissions platform. One important difference is that an origin user 10, 12 can "have" clone users 14, 16, 18, 20 related to it, and every clone user must (by definition) "belong" (e.g., be assigned) to a specific origin user, while an origin user does not belong to any other user.

In at least some implementations, a clone user is said to belong to an origin user in the sense that the particular set of features for which the clone user has permissions is always identical to the set of features 22, 24 for which its origin user has permissions. If the permissions of the origin user are changed, the permissions of the clone user are immediately and similarly updated to be identical to the new permissions of the origin user. This in effect makes every origin user and its clone users into a group that can be thought of as corresponding to a role of the enterprise (i.e., with the permitted feature set supporting users that have the corresponding role to fulfill that role for the enterprise.)

An origin user and all of its clone users can be thought of as a group 26, 28 of users all of whom have the same permissions for features of the application. In that sense, such a group can be associated with a role within the enterprise (that is supported by the permitted feature set of the group)) 30, 32 in the enterprise 34. Within the permissions platform 8, every user has a name 36, 38. The permitted feature sets 22, 24 for different origin users are typically different. Permitted feature sets for different origin users could be specified to be the same but they are not the same as a result of automatic inheritance of a permitted feature set from another origin user.

We use the term "permitted feature set" to include, for example, any one or a combination of any two or more of the features provided by an application, including features that are exposed through a user interface. As noted later, features exposed through the user interface can include not only controls that appear in the user interface but also content such as data fields that are displayed to the user as well as the ability to reorganize the layout of the user interface controls and content (including hiding data fields from users).

We use the term "origin user" broadly to include, for example, any user whose permitted feature set (or at least a subset of the permitted feature set) is not automatically governed by the permitted feature set of another user.

We use the term "clone user" broadly to include, for example, any user whose permitted feature set (or at least a subset of the permitted feature set) is governed automatically by the permitted feature set of another user.

We use the term "user" broadly to include, for example, any person who is a user of any of the features of an application, including an origin user or a clone user.

Each user has a unique user ID and a unique user name stored in the permissions platform. The user ID of an origin user can be created to correspond to a role of the origin user in the enterprise (for example, "radiologist"). When a clone user of that origin user is created, the permissions platform associates the clone user with the origin user in the database of the permissions platform and implicitly with the user ID that corresponds to the role of the origin user. For example, if an origin user is added to the permissions platform with the user ID of "Site Admin", and a clone user is added under that origin user, the user IDs and the user names of the origin user and the clone user are different. When user information about the clone user is displayed in the user interface, the clone user is identified as a "Clone of Site Admin".

Although all of the users in a group share the same permitted feature set (thereby implying a corresponding role that associated physical users have in the enterprise), each of the origin users and clone users is associated in the permissions platform with a different physical user 40, 42, 44, 46, 48, 50 who is affiliated with the enterprise. Therefore, in a simple example, a small number of origin accounts can be created each with a unique separate and independent feature set that corresponds to a role that the physical users associated with these origin users and their clones require in support of their work within the enterprise.

However, because an administrator or other user who has the permission to do so can assign any arbitrary set of features to any group and can create any arbitrary number of groups with any arbitrary respective roles, without requiring involvement of the developer, the permissions platform enables a rich and easy to use mechanism for controlling permissions for an application used by an enterprise.

Unlike many permissions management systems, the permissions platform that we describe here does not require a cumbersome hierarchical description or management of the roles of an enterprise. Rather only two levels are required: origin users and clone users. With that simple structure, any number and organization of roles can be defined and changed at any time by an administrator without requiring the involvement of a developer. And, because any arbitrary feature set can be assigned to any group (role)—by being assigned to an origin user and then creating clone users that belong to the origin user—and changed easily and at any time, there is no limit to the flexibility of the permissions platform while retaining simplicity of user and group administration.

The permitted feature set for the users of each group (an origin user and its clone users) can be quickly and easily changed by changing the permitted feature set of the origin user, and the members of each group can be easily and quickly changed by changing the designation of users (clone versus origin) and the identity of the origin user to which a clone user belongs. As many new groups as are needed (e.g., an unlimited number) can be created and any degree of subtlety of the distinctions in permitted feature sets among the different groups can be achieved. In theory an administrator can use the permissions platform to define an implicit hierarchy of users at more than one level of roles, but doing so is not required and may create undesirable complexity. The permissions platform does not in any way constrain users to a hierarchy.

The features to which the permissions platform can be applied can include both features of the application with which the permissions platform is associated or of which it is a part, and can include features of the permissions platform itself, such as permissions management features. The features to which the permissions platform can be applied could in theory include every feature with respect to which a user can be involved or with which a user can interact. In many cases, the features to which the permissions platform is applied are features that are exposed through a user interface. We sometimes refer to them as interface features. Interface features can include user interface controls such as buttons or drop down menus or text entry boxes, to name three. Features also can include interface data features that expose content to the user and enable the user to navigate the content, such as data tables that display rows and columns of data elements to a user such as tables containing data entries and related navigation features such as scrolling through content data. Interface features can also include features that enable a user to change the layout of elements in the user interface, for example, to change the order of fields of a table, or to move a button from one location to another on the interface.

As explained later, the features to which the permissions platform can be applied can include the kinds of features that are normally only exposed in conventional systems to an administrator or even only to the developer or original distributor of an application. Because these permissions management features are susceptible to the operation of the permissions platform, unusual and useful permission management approaches can be exposed to the user in the same user interface in which the features of the application are exposed.

For example, effectively any role within an enterprise (including administrator and administrator-like roles) can be accommodated and made flexible. Even features that enable a user to create a new origin user or a new clone user or to save a worklist layout can be managed. In some cases, an administrator could be an origin user (or clone user of an origin user) who could invoke only the feature to create a new clone user, but not to invoke the feature to create a new origin user. Or a user who does not to have any authority to manage either clone users or origin users could be denied exposure or access to a "manage users" feature through the user interface.

A user who cannot save any changes to the user interface features of the user interface pages that are served to her cannot add or remove the user interface controls associated with any feature of the application or the permissions platform and cannot change or save changes to the layout of the user interface pages can be called a kiosk user. An example of such a kiosk user might be a clone user of an origin user named "desk clerk".

To summarize, in many implementations, there are two key principles that govern the operation of the permissions platform: 1. Every feature of the application and the permissions platform can be assigned to any given user, and 2. There are only two kinds of users: origin users and clone users.

Because of this simplicity, any user who knows enough about the workflows and roles of an enterprise can learn to be an administrator in a few minutes, and such a user faces no constraints as to the constituent features of the permitted feature sets that can be assigned (since they all can be, individually) or how many groups can be formed. In addition, a developer need not consider or predefine workflows or roles or permitted feature sets that can be assigned to those roles. Those definitions can be made by the administrator of the enterprise and changed easily and at any time. In addition, the enterprise can easily determine how many different groups (roles) it wishes to establish and the number and nature of the features that it wishes to allow users to manage. All of this is achieved by the permissions platform while maintaining simplicity of management because the permitted features set for any number of clone users (up to a very large number) can be changed at once by simply modifying the permitted features set of the origin user When an application that uses the permissions platform is first put into service, an "initial origin user" (or more than one) is created and a physical user is associated with each of those origin users. Those initial origin users can be given permissions with respect to every feature of the application and permissions platform to which users are ever to have access. The initial origin users could be employees of an enterprise that has developed the application or the permissions platform or both to be distributed to one or more customer enterprises.

When the permissions platform and associated application are distributed to a customer enterprise, one of the initial origin users can create an "initial enterprise user" (or more than one) for that particular customer enterprise. The permitted feature set for such an initial enterprise user can be selected so that the physical user or users associated with that initial enterprise user can have access to a broad range of the features of the application and of the permissions platform. That permitted feature set might exclude only a very small number of features of the permissions platform that necessarily should be exercisable only by employees of the enterprise that developed the application or the permissions platform or both.

Thus, the permissions platform enables any authorized user who has the same or larger scopes of fields and features and of institutions than does another user to potentially control the scopes of those other users if the authorized user has a permitted features set that allows her to edit other users. The administrator can control the permitted feature set of the authorized user accordingly based on workflows, responsibilities, and trust levels.

When the permissions platform and the application are distributed to more than one customer or enterprise, each of the customers or other enterprises typically will insist that only people affiliated with it can be users who will have access to features of the application with which the permissions platform is being used. One way to accommodate this requirement is to operate the permissions platform and the application on a discrete separate server for each of the customer enterprises. Under a different approach, multiple enterprises or other customers can use the permissions platform and application running on a single server in what is sometimes called a multiple tenancy mode.

In order to enforce a multiple tenancy mode, one feature of the permitted features set for the initial origin users can enable a permitted user to define an institutional scope for each of the customers or other enterprises that will use the permissions platform and the application. The permissions platform and the application can be arranged so that data that is private to an enterprise can only be accessed, viewed, or used by authorized users affiliated with that enterprise, that is, users for whom the institutional scope aligns with the enterprise with which the users are affiliated. Analogous features can be included in the permitted feature sets for the initial enterprise users to enable them to arrange sub-institutional scopes to manage sub-multiple tenancies. For example, a group of affiliated hospitals may constitute an institution at the top level of institutional scope. Users for whom the institutional scope is of the entire group of affiliated hospitals will have permitted feature sets that enable them to view private data associated with all of the affiliated hospitals. Other users may have institutional scopes that are limited to individual affiliated hospitals or subsets of them and those users will have permitted feature sets that enable them to view only private data associated with those individual affiliated hospitals or subsets of them.

When the permissions platform and application are provided to an enterprise, the initial enterprise user can include a set of "seed origin users" that can serve essentially as templates for use by the initial enterprise user. Seed origin users can have standard roles and corresponding permitted feature sets that might be typical of those that the enterprise may wish to use. For example, if the permissions platform and application are to be delivered to a hospital, the seed origin users could include origin users whose roles are LMS Admin, Client Admin, Site Admin, Clerk, Technician, Resident, Attending, Chief Radiologist, and Chief Technologist and whose permitted feature sets are typical of people who have such roles in hospitals. The choice of seed origin users can be different for each enterprise and can be updated at any time without the help of a developer.

We use the term "user interface features" broadly to include, for example, any such feature, such as user interface controls, layouts and organizations and appearances, and content, among other things.

As shown in FIG. 3, the permissions platform 60 can operate as part of or as an adjunct to any application 62. An interactive user interface 66 is exposed by the permissions platform 60 or the application 62 to users 64 of the application, for example, by serving HTML pages 68 over the Internet 80 to a browser 72 running on a device 74 associated with the user. (Other approaches to exposing the user interface to the user could also be used. The device 22 could be a mobile device and the user interface could be exposed to the user of the mobile device through an app running on the mobile device.)

In implementations that use HTML pages, the permissions platform can take advantage of features of the HTML5 protocol with respect to the serving of the pages.

Therefore, the permissions platform or the application or both have a page server 90 capable of serving dynamic pages in response to the operation of the application and in response to requests received from the browser 66.

The permissions platform or the application or both has a database 92 that contains information about the authorized users of the application. In some examples, when a user 64 logs in through the browser to the application and her credentials are authenticated, the permissions platform or the application or both selects and manages all of the user interface features on pages 68 that it serves to that user through the browser so that the only user interface features to which the user has feature access and can use are features included in the permitted feature set with which the user is associated in the database, either as a clone user or an origin user.

We use the term "feature access" broadly to include, for example, the ability of a user to engage, invoke, activate, select, observe, or in any other way interact with a feature in a way that is intended by the permissions platform or the application or the developer. For example, the feature may be a process that is part of the application and can be invoked by interaction of the user with a control on the user interface. The user has feature access to that feature when the user is able to interact with the control in a way that invokes the feature, such as by clicking a button or selecting an item from a drop-down menu. A user who has feature access may be exposed in some lesser sense to a feature of the application through the user interface but not be able to invoke it. In such cases, for example when a drop down menu item is grayed out. In another example, if a table is presented through the user interface that contains actual data items that can be viewed by the user, we can say that the user has feature access to the data items. Thus both viewing and invoking can be part of feature access.

As noted earlier, the permitted feature set for a user can include an ability to change the organization, appearance, or layout of pages that are served. For example, a particular origin user may have a permitted feature set that enables that user to move controls to new locations on pages. In some cases, a permitted feature set includes features that are administrative with respect to permissions management, such as the ability to create new users. As mentioned earlier, some users may have the ability to remove controls related to that feature from the user interface. Thus, some users can have permitted feature sets that enable them both to interact with the application in their roles within an enterprise and at the same time enable them to interact with the permissions platform to perform permissions management functions. Some users can have permitted feature sets that enable them only to interact with the application.

If one considers the entire set of controls, content, and interface layout features that an application and the permissions platform are capable of exposing to users of dynamic web pages, the permissions platform enables administrators (and actually any user, depending on his permissions) to easily and quickly define a subset of controls and content elements and layout features that will appear and be active for any of the individual users, while other controls and content elements will not be exposed to the user (even to a user who tries to spoof the system) or will be exposed to but not made invocable by the user.

In an example of applying the permissions management features of the permissions platform, in the context of a medical report related system, several users could have the common role of "chief radiologist". One would be the origin chief radiologist and the others would be clones of the origin user. However, it would not be necessary for all chief radiologists to belong to that group. Two different chief radiologists could be made origin users with two different finely tuned permission feature sets.

Information about the relationship of physical users to origin users and clone users and the permitted feature sets of each of them is maintained in the database 92.

In some examples, a schema for at least part of the database 92 could be defined as follows:

Operational Fields:
  Audited events (e.g., report access times, statuses, system logging)
  Institutions (Labels, AE [application entity] Titles, codes, PDF templates, fax numbers)
  Operating Sites (Labels, AE Titles, codes, PDF templates, fax numbers)
  Devices (Labels, AE Titles, codes, PDF templates)
  Institution or Operating Site (Points of contact)
  Report statuses and sequencing
  Auto/manual fax
  HL7 [health level seven] import and export
  Attached imagery and paperwork
  Decision support system (pages and content)
  Report exporting to clients Fields and Features (FAF, Referring to User Interface Features, Content Display Features, and User Interface Layout Features)
  Field and feature list
  Field and feature definition tables: (e.g., global localization, descriptions, attributes, dependencies)
  Field to page mapping (defines where and which FAF groups are allowed to appear on the UI)
  Field, feature, and layout templates
  Active template attributes
  Custom user defined fields
  RIS [radiology information system] fields (study, series, patient, reporting, addendums)

User Level Field and Feature (FAF) Management.
  User←-to-→FAF scope mapping (account type [origin user] clone user] and flags)
  User defined page layouts
  User defined field and feature localization
  Per origin institution and operational site scope User Accounts:
  Access control (User ID→Password mapping)
  User accounts (Name, email, telephone, etc.)

The permissions platform 60, the application 62, the page server 90, and the database 92 can run on one or more servers 100. When the server is preparing to serve a page 68, it knows the identity of a physical user 64 who is working at the browser (among other ways, because the user has logged in and the user's browser has sent a request to the server). The server knows which origin user or clone user is associated with the physical user, and it can look up in the database 92 the user's permitted feature set and details about how the user has configured the user interface. The server, in constructing the page to be served, dynamically constructs a page that corresponds to the permitted feature set and user's intended layout of the page. The server excludes from the page features that are not within the corresponding permitted features set. Attempts by the physical user to spoof the server into exposing the unpermitted features can be thwarted by the server because it knows who the user is, can associate any incoming bogus requests with the user, and can continue to expose to the user only features included in the permitted feature set.

Adding or subtracting a physical user to or from the operation of the permissions platform is as simple as associating or disassociating the physical user with the appropriate origin user or clone user. Changing the permissions that are part of the permitted feature set of a user is also simple.

Details of an example user interface based on a permissions platform are shown in FIGS. 4 through 21.

Figure 4:
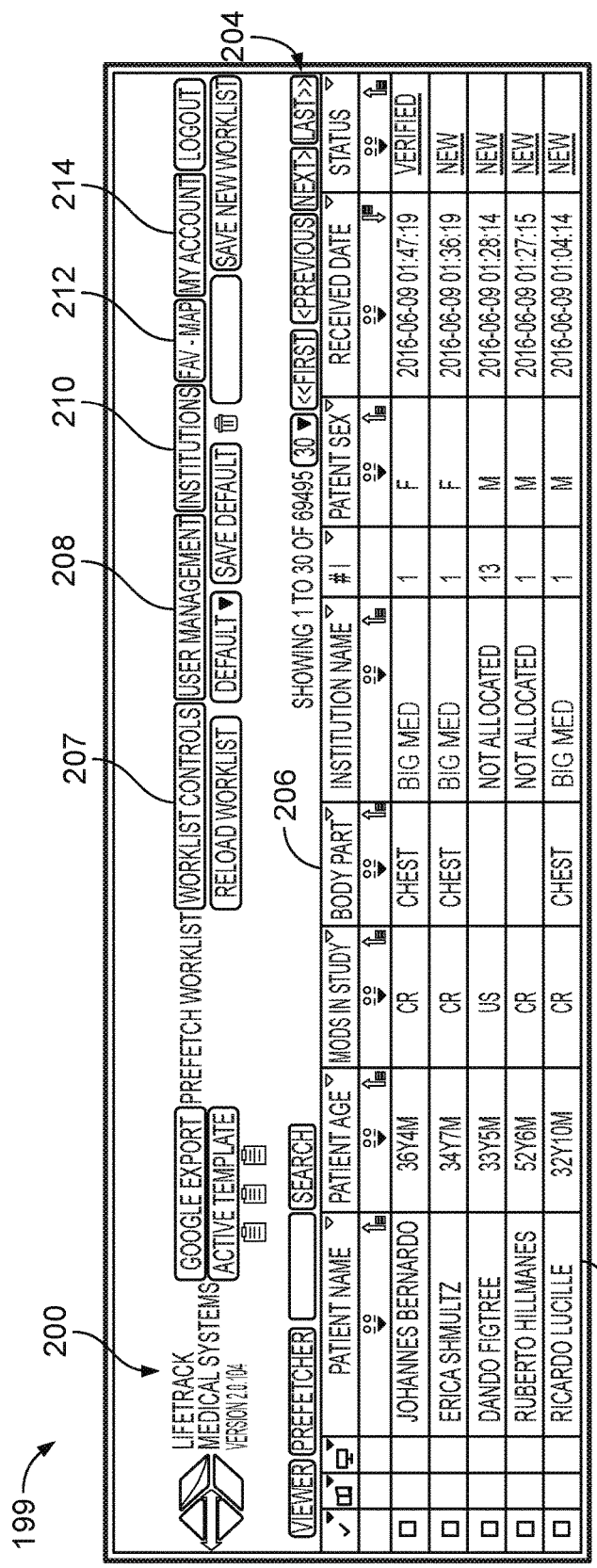

As shown in FIG. 4, a page 199 of the user interface of the permissions platform and the application 200 presents a table 202 that displays rows each related to a particular case under consideration. In this instance, the cases relate to patients for medical care requiring the attention of a radiologist. Each row in the list contains data items in fields represented by columns 206. The data underlying the table can be navigated using controls 204 to enable a user to view any of a potentially very large number of records stored in the database. In the upper right-hand corner of the page are additional controls that enable the management of users and features, among other things. The user management button 208 enables a user to manage users of the permissions platform in the application including their permissions. The institutions button 210 enables users to define and manage the institutional context in which the permissions platform in the application are being used. A FAV-MAP button 212 enables the user to modify the Features AVailable to the user. A user for whom the FAV-MAP button appears on the user interface has significant power in that she can modify her scope and the scope of other users. Additionally there is a button on the FAV-MAP dialog that allows her to add new custom data fields to the data. The my account button 214 enables a user to review and take actions with respect to her account profile (including updating the user password).

Figure 5:
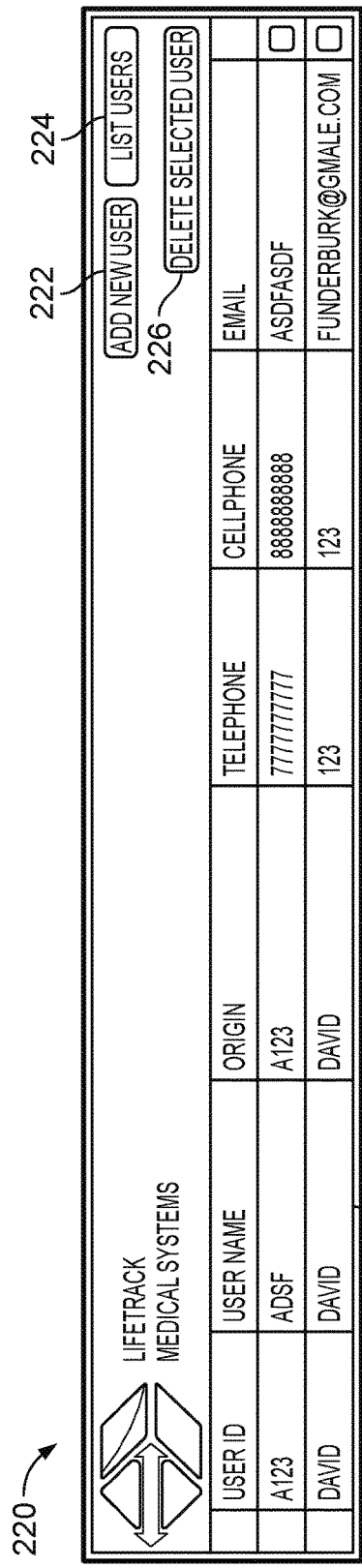

The page 220 shown in FIG. 5 is reached when the user invokes the button 208 of FIG. 4. The page 220 includes a list of users and data items about the users organized in fields. A button 222 enables the user to add a new user and a button 224 enables a user to view a list of users (such as the one shown in this FIG. 5). A button 226 enables the user to delete a selected user from the list.

Figure 6:
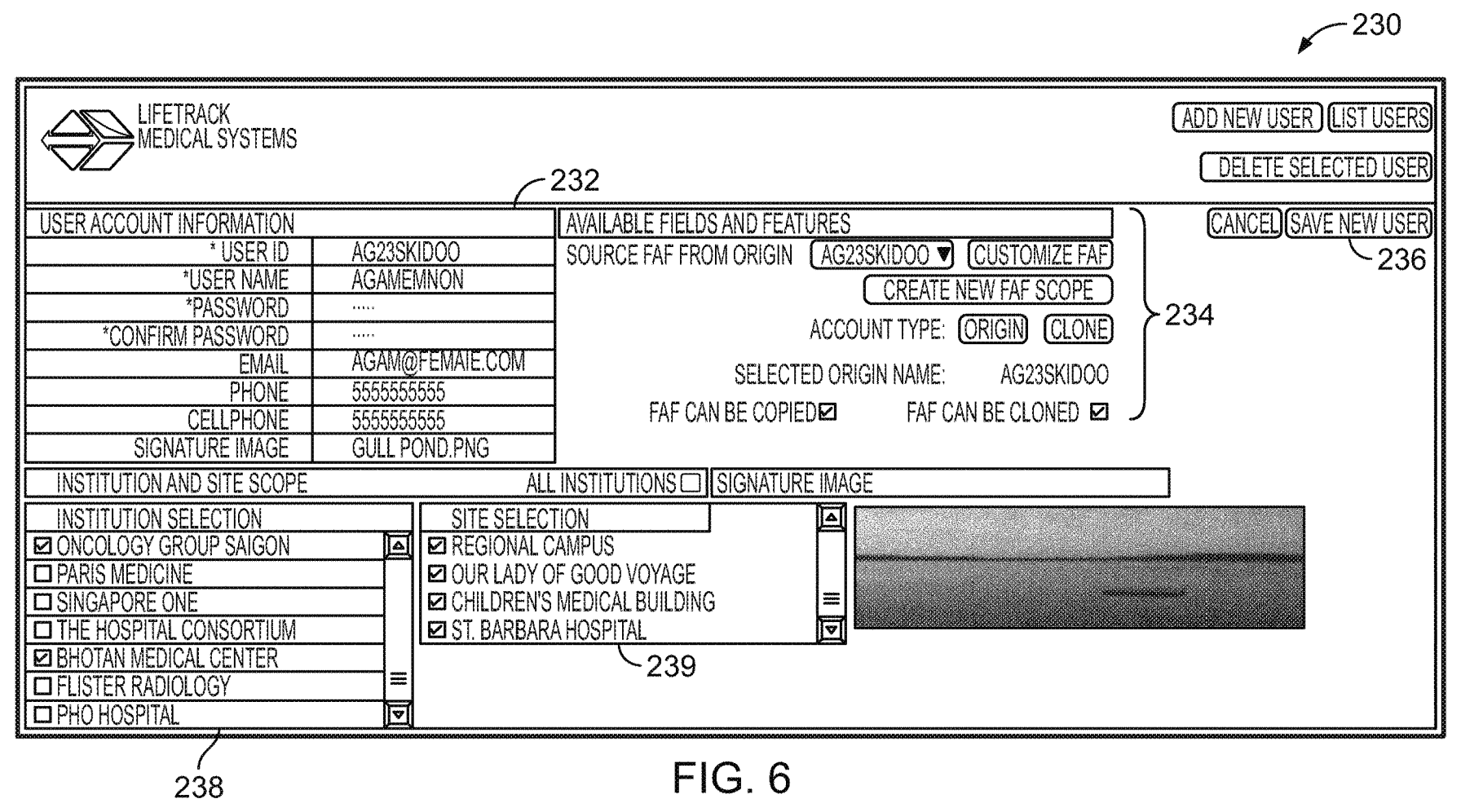

When a user invokes the add new user button of FIG. 5, the page 230 shown in FIG. 6 is presented. This page enables a user to add another user, added information related to a user, or simply view information associated with the user.

The page 230 also appears when a user invokes one of the records on the list 228 in FIG. 5.

FIG. 6 is organized to include user account information 232, that is, profile information about the user; information about institutions 238 and sites associated with the institutions 239 with which the user is linked in the permissions platform; and controls 234 that enable a user to control the permissions of the user with respect to at least some of the interface features of the permissions platform and the application. All of the information on FIG. 6 can be initially entered when a new users created (after which the save new users button 236 is invoked); and the information can be altered at any time by a user who has permission to do so. In FIG. 6, the interface features are referred to as "fields and features" referring to the fact that they can control both interactive user interface controls and content (e.g., data items) that the user will have permission to view and work with.

Figure 7:
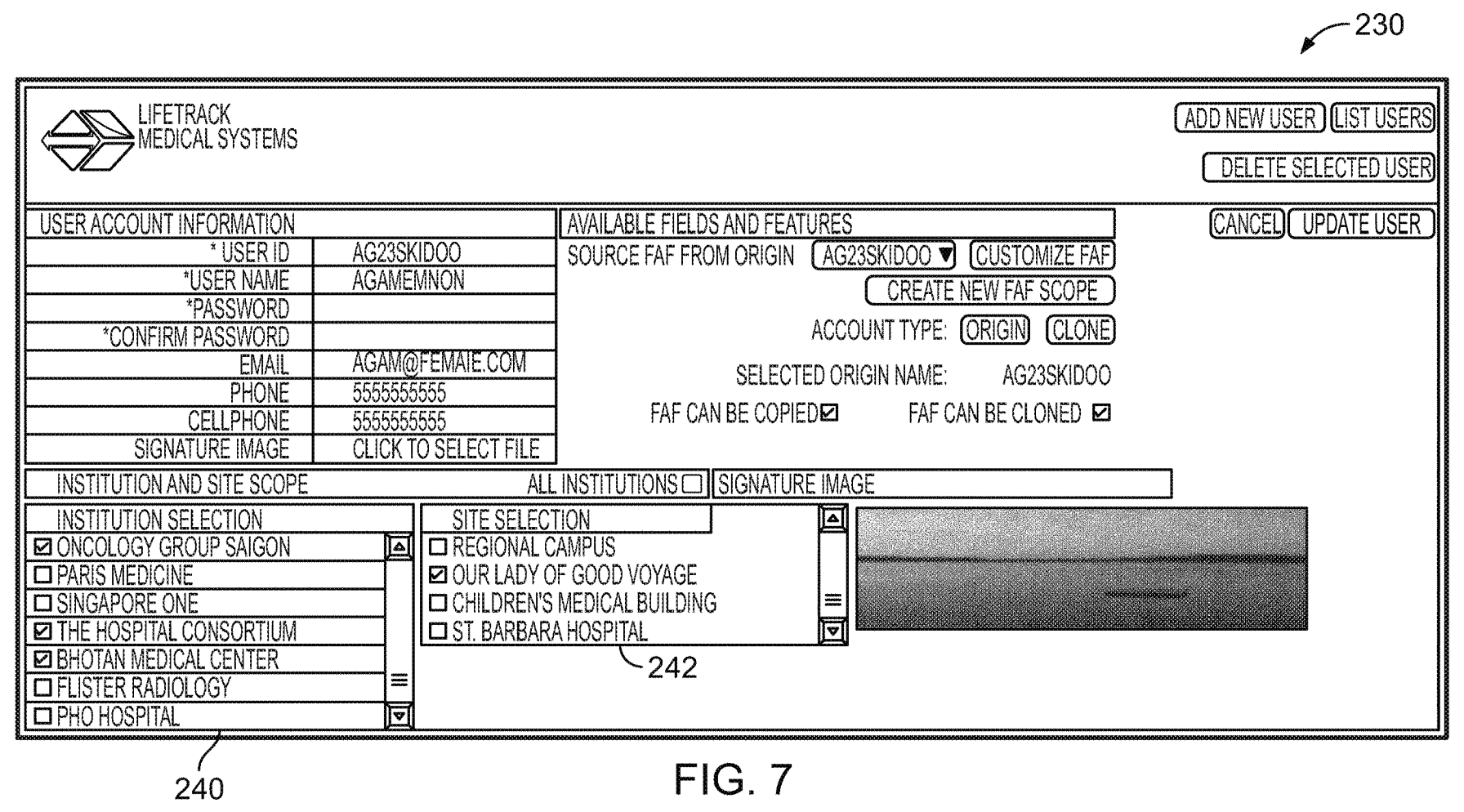

The institution selection list 238 Identifies institutions whose employees, for example, may have access to content presented through the user interface. The user being defined in FIG. 6 belongs to the institutions marked by check marks in the list 238. Each of the institutions may also have a corresponding set of one or more sites which are displayed in the list 239. The check marks in list 239 identify the sites with which the user is associated. The content of each of the institutions and sometimes the content of each of the sites associated with each of the institutions is private to the patients at the institution or site and hence to the institution or site. Therefore, only users associated with selected institutions or sites should have access to content presented with respect to patients at those sites. In this sense, the institution and site selection list 238 and 239 define an institution and site scope for the content that can be used or manipulated by the user. FIG. 7 shows updated list 240 and 242 in which changes have been made to the scope.

The controls 234 in FIG. 6 include two buttons labeled origin and clone that refer to the type of user, either an origin user or a clone user. The user must be one or the other and the buttons control which type. Below these two buttons is the selected origin name. As discussed earlier, every origin user and all of the clone users that belong to that origin will share a common origin name, which is shown on this line. In the line below that line, are two check box controls that indicate whether the fields and features of this user can be copied in creating another user and whether these fields and features can be cloned in the creation of a clone user. At the top of the set of controls 234 the user is able to click a drop down button to select or view a permitted feature set of another identified user when the user wishes to create a new clone user. The user can customize that other user's permitted feature set by clicking the customize FAF button. The button titled create new FAF scope can be used to start the creation of a new permitted feature set.

When the user by invoking the button next to the title source FAF from origin on FIG. 6 and then clicks the customize FAF button, she is presented with the list of fields and features shown in the page 252 of FIG. 8. FIG. 8 includes a list 254 of every possible feature of the application and the permissions platform that could be the subject of a permission for the user (only a small list of the fields and features are shown in FIG. 8). The fields and features that are actually shown in FIG. 8 are fields and features of the application. Other fields and features could be those of the permissions platform itself. In each row of the list, a field or feature is identified in the first column using the variable name assigned within the software. The second field contains the name of that feature is used in the user interface. The third field would contain a tooltip to be displayed when a user causes the pointer to hover over the control associated with the feature. The fourth column identifies whether the feature will be within the permitted feature set of the user. Add indicates that the feature is not yet in the permitted feature set. Remove indicates that the feature currently is within the permitted feature set.

Figure 9:
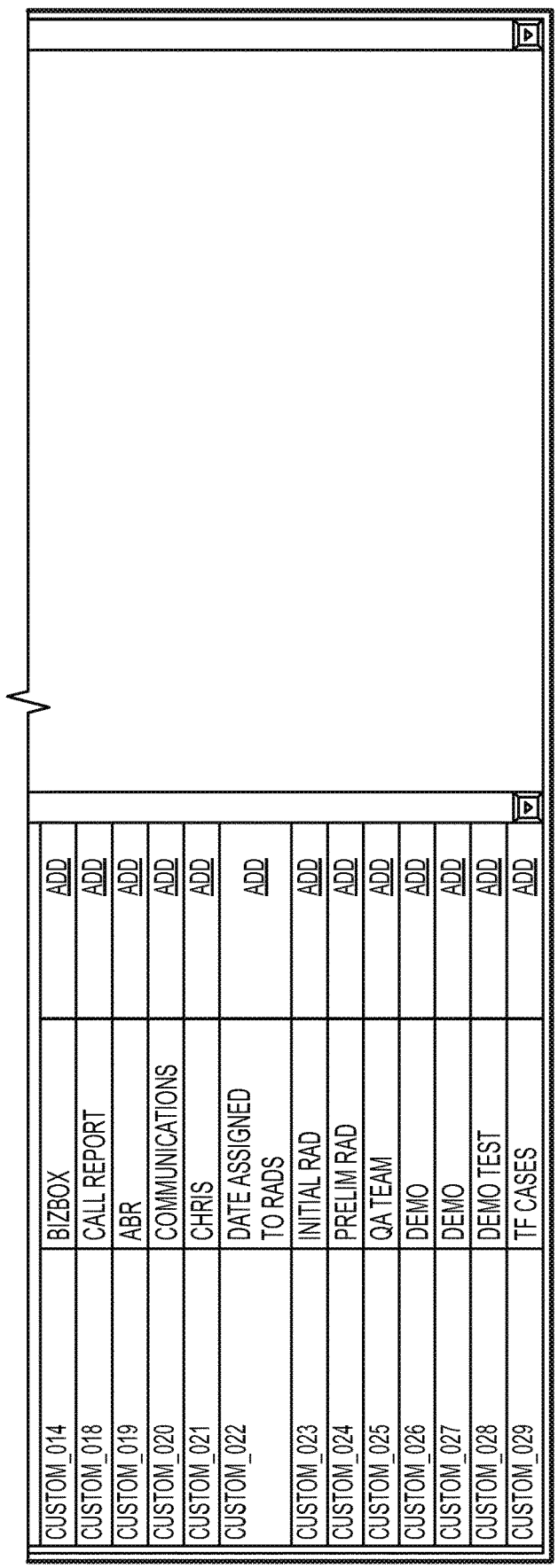

FIG. 9 illustrates the same page 252 that is presented when the button of FIG. 6 is invoked. Here, none of the features has yet been included in the permitted feature set.

When the user invokes the button 207 of FIG. 4 (or right clicks within the FIG. 4), the page 260 appears including the worklist controls dialog box 262. The worklist controls dialog box contains a list of features of the application that are exposed to the user through the user interface. The dialog box 262 enables the user to identify the features that should appear on the user interface, by checking the checkboxes. Unchecked features will not appear on the user interface. For example, the institutions button 210 of FIG. 4 can be made to appear or be hidden depending on whether the checkbox 266 has been checked or unchecked. This effect can be seen in FIG. 11 in which certain of the features have been unchecked such as the institutions feature checkbox 270 and therefore no longer appear among the buttons in the button set 282.

Figures 12, 13:
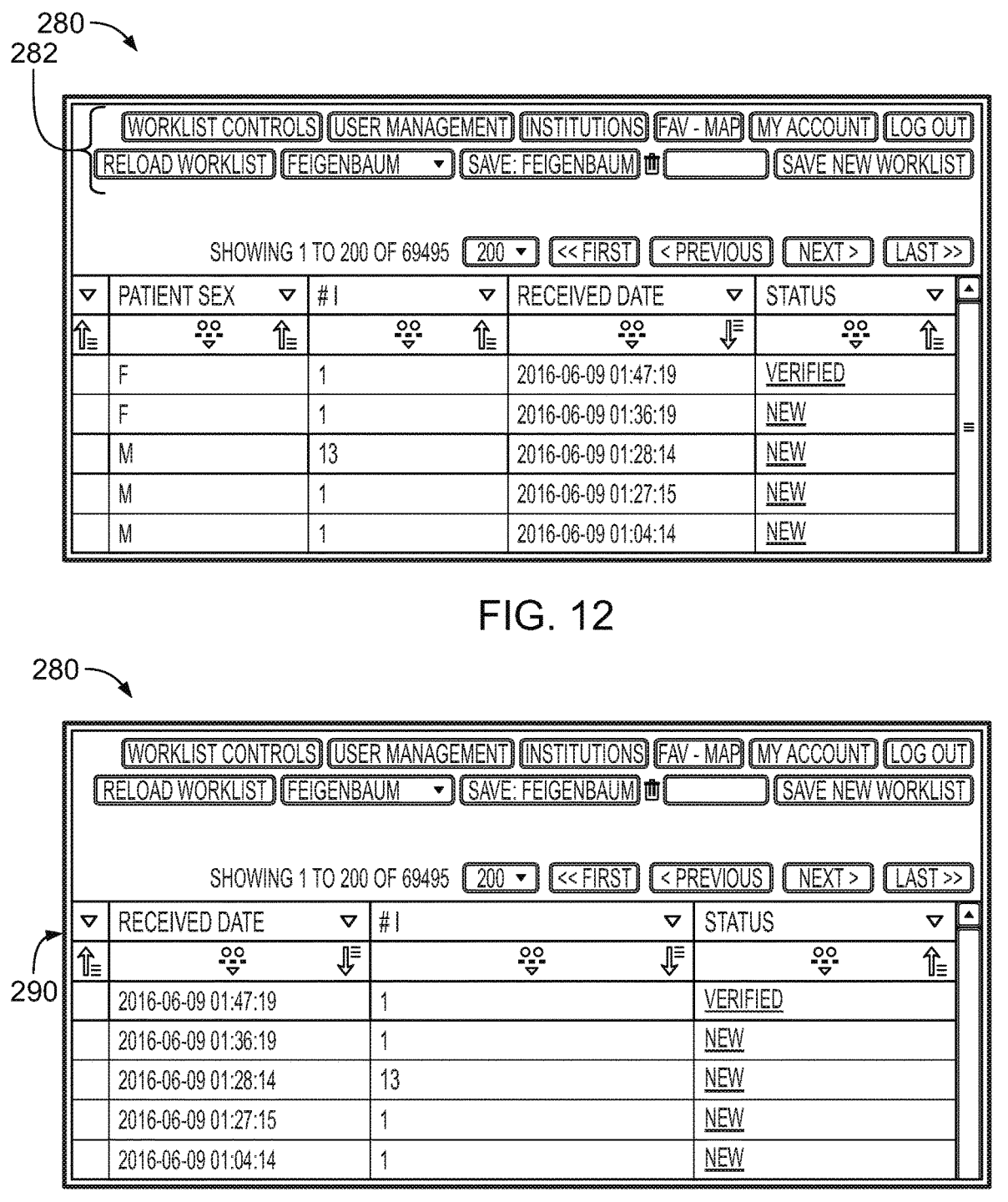
Figures 14, 15:
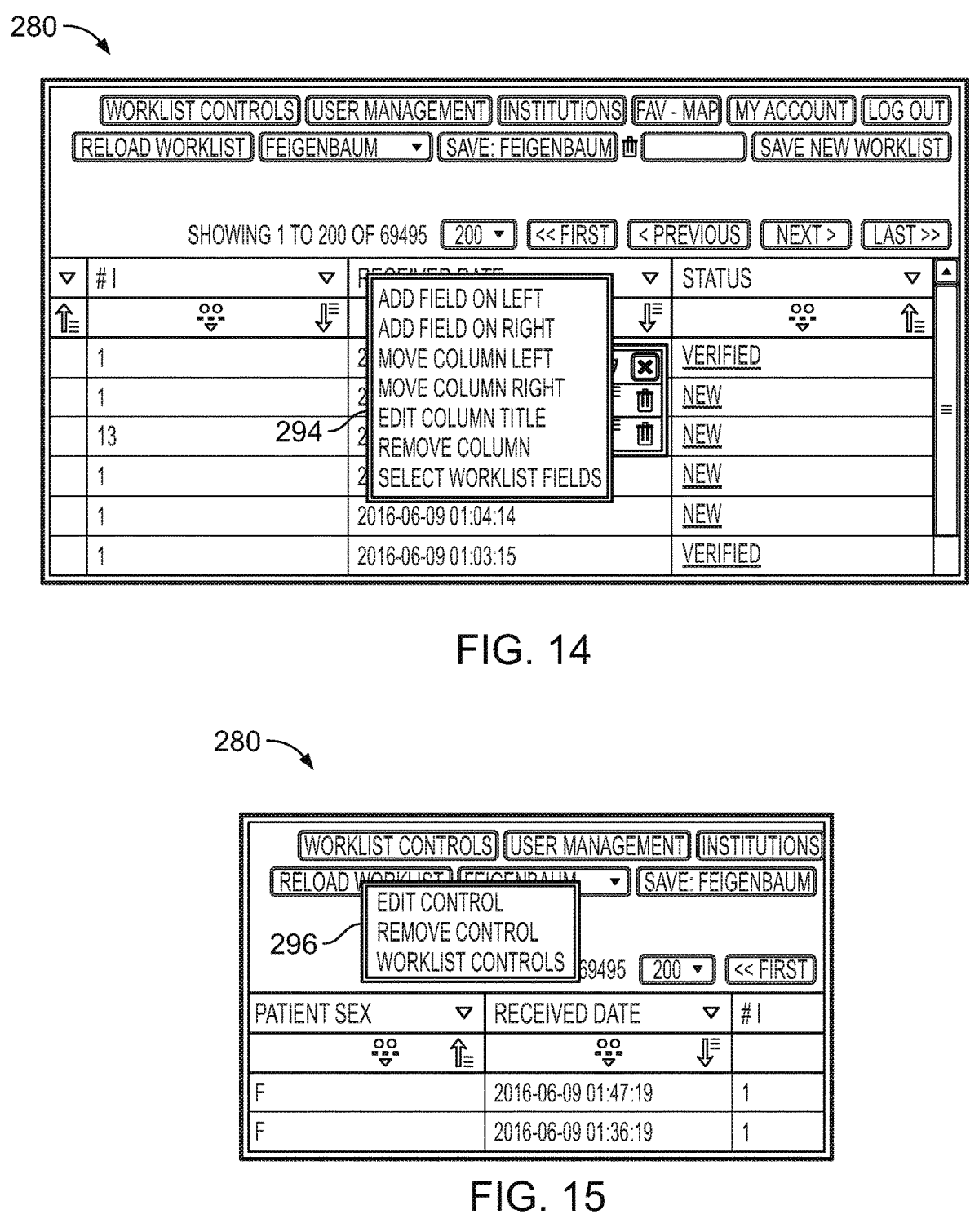
Figures 16, 17:
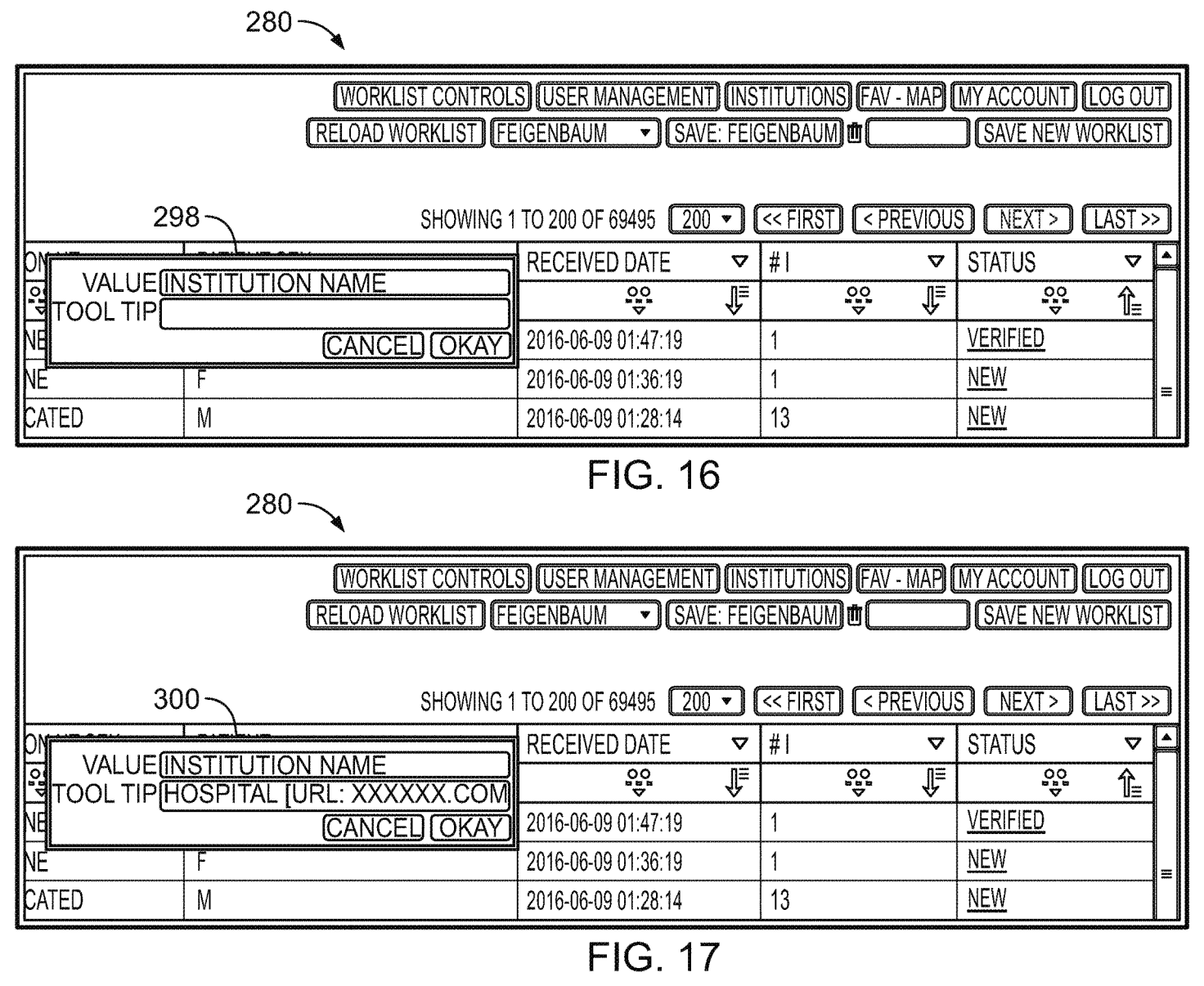
Figures 18, 19:
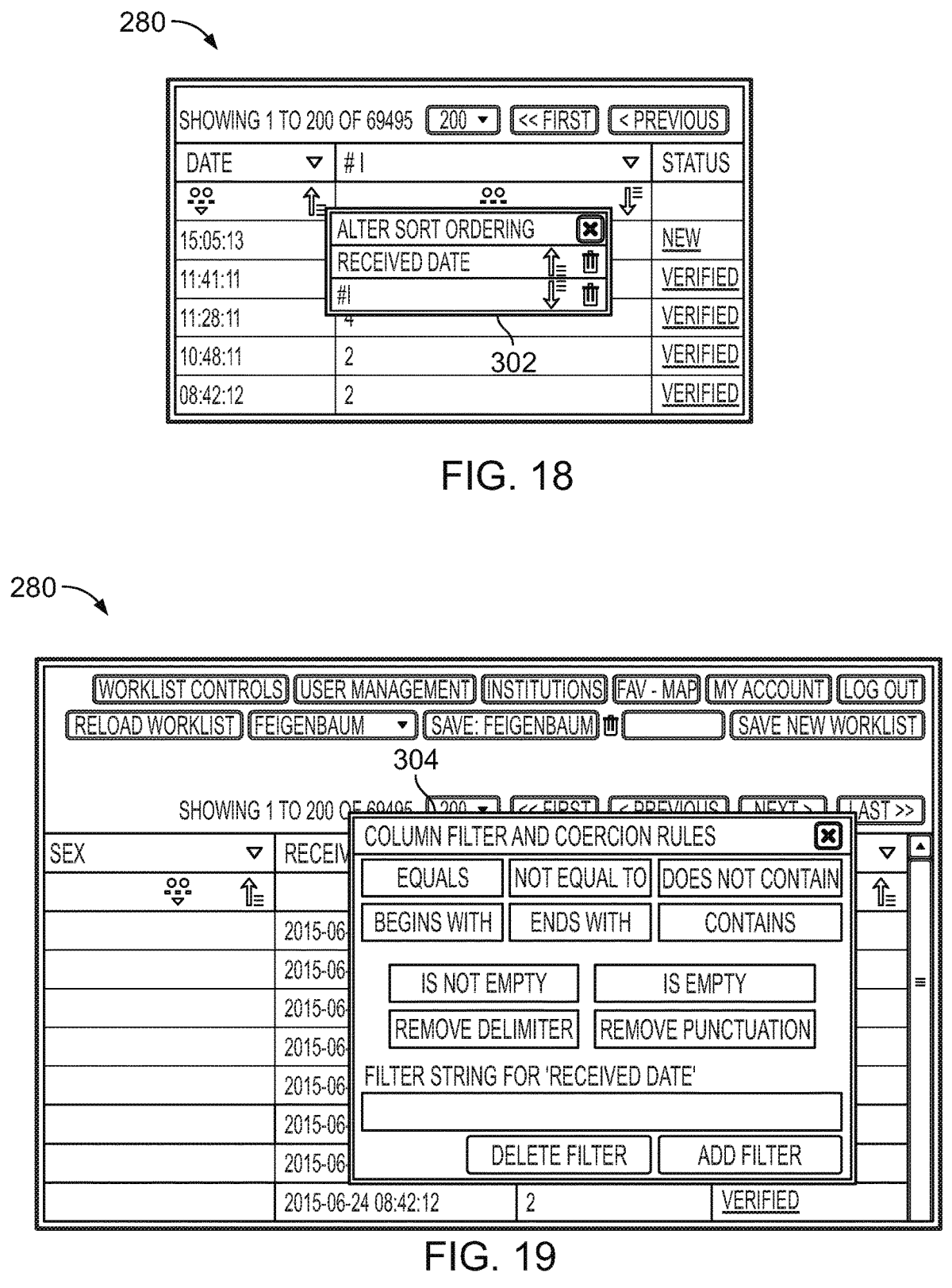

The user can also control aspects of content that are displayed in a table, including the location and presence of various fields, the ordering of data within the table and the filtering of data within the table. This is illustrated in FIGS. 12 and 13 in which the column received date has been moved to the left of the column # I. FIG. 14 illustrates how columns of the table can be manipulated by right clicking on the field title to cause the menu 294 to appear. Similarly, by right clicking on any of the controls and the upper right hand part of the page 280, the user can edit the control, remove the control, or view the list of work list controls using the menu 296. If the user invokes the menu item "edit control" the dialog box 298 FIG. 16 appears. This enables the user to change the value of the control and to provide a tooltip, including a URL as mentioned earlier and illustrated in FIG. 17. FIG. 18 illustrates the menu 302 that can be used to alter the sort order. FIG. 19 illustrates the menu 304 that enables control of filtering features.

Figure 20:
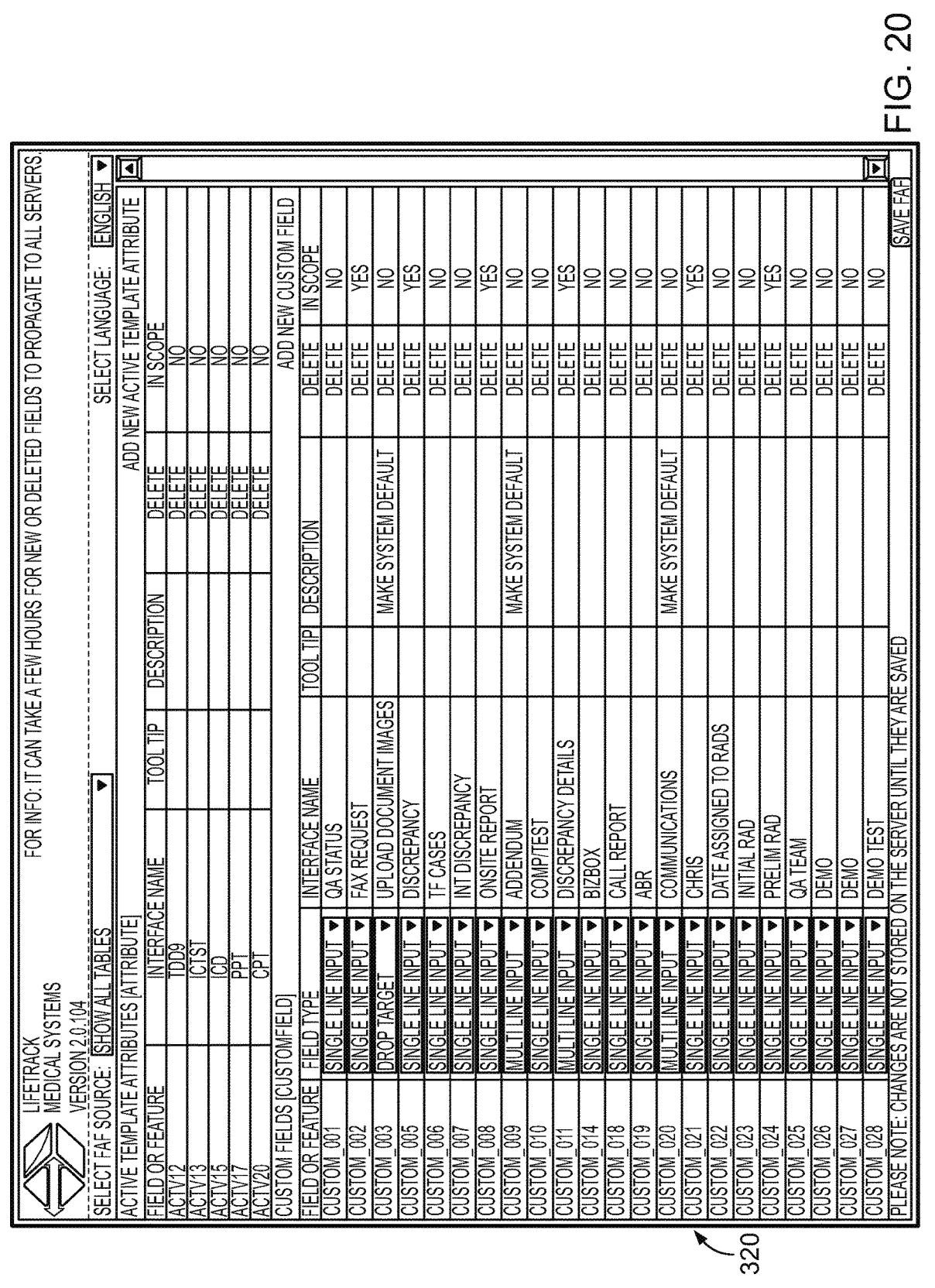

When the user invokes the button 212 of FIG. 4, the window 310 of FIG. 20 appears. When the user selects an origin user in this window, she can view and alter the fields and features (the permitted feature set) that will be available to the selected origin user (and therefore also the clone users of that origin user).

Figure 21:
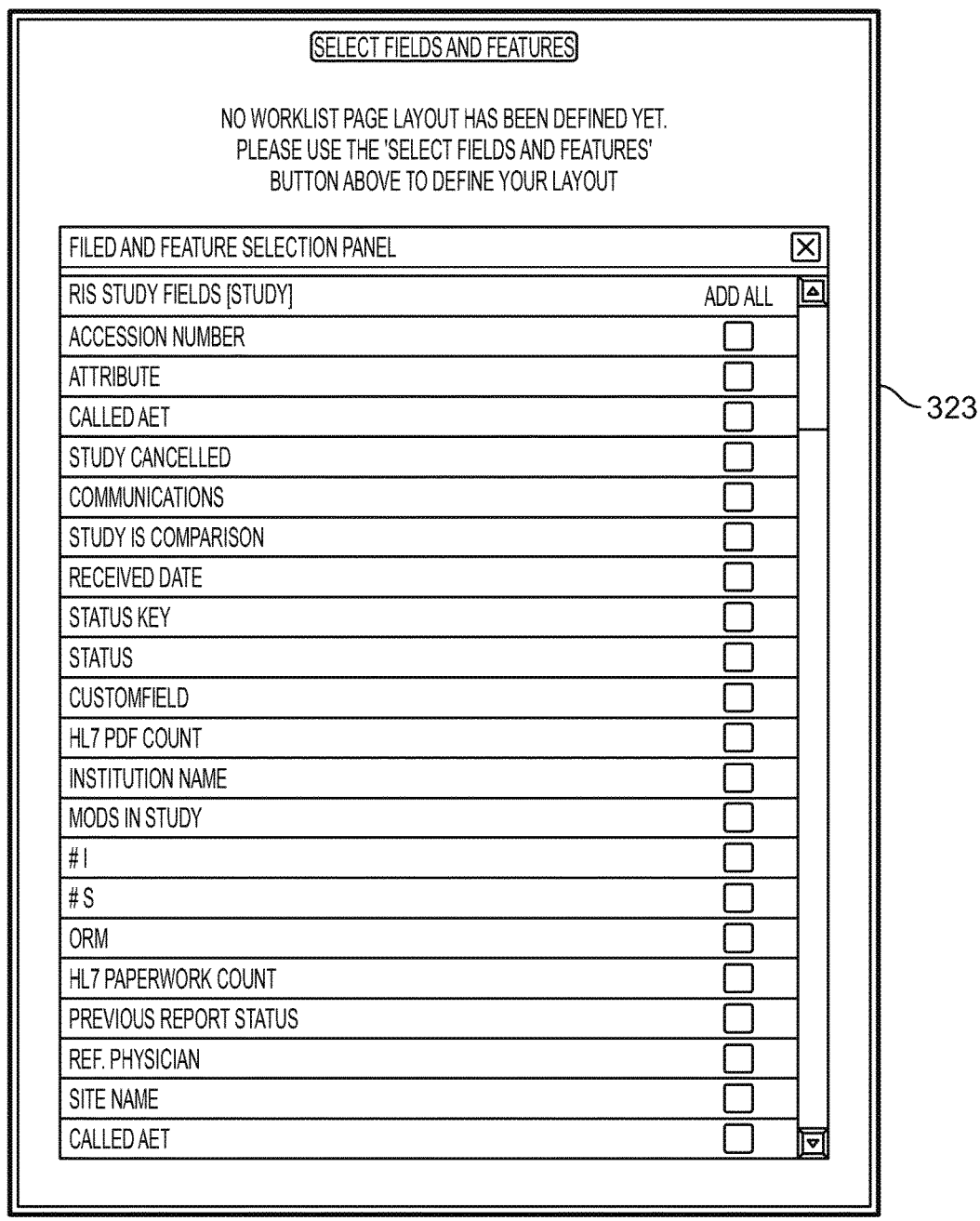

When the button labeled add fields and features 313 of window 310 is invoked (which might typically be exposed only to users who are affiliated with the developer of the permissions platform and are configuring an application for a particular customer), the window 320 of FIG. 21 appears. This enables the user to view fields and features available in the permissions platform and application. A user for whom button 313 is available may also change the language localization as well as customize the interface control names and tool tips for any specified language at the system level. It also allows a user with this button 313 to administer the availability of specific fields and features available to specific origin users. The two windows shown in FIGS. 20 and 21 can be used to add new fields and features and languages to any customer's server and system without violating the paradigm that even low-level system administrative functions are controlled by permissions to regulate who within the development enterprise have which permitted feature sets. Configuring and updating the system for a customer is achieved through the same user interface and permissioning system that we have been discussing, rather than by having developers directly modify elements of the database to add new fields and features. An added benefit is that, within the development enterprise, once a new function has been developed any of the permitted users of the development enterprise to whom FAV-MAP button and the Add fields and Features button are exposed, could make the new function available to any customer quickly and easily.

When the user invokes any of the records shown in the table of FIG. 4, for example by double-clicking on the record, the window 321 of FIG. 21 is displayed. A dialog box 323 includes a list of fields that can be included in the table by checking the related checkboxes.

Whenever an origin user who is permitted to do so alters any of the features of the permitted feature set associated with that origin user, the permitted feature sets of all of the clone users who belong to the origin user are also automatically and immediately changed. For example, if an origin user changes the arrangement of the table of FIG. 4, all of the related clone users will be presented with tables organized according to the new arrangement.

Other implementations are also within the scope of the following claims.

For example, the permissions platform could be useful in conjunction with a wide variety of applications in a wide range of fields and industries, such a customer relationship management and airline reservations, to name only two.

The invention claimed is:

1. A computer-implemented method comprising:
displaying a user interface page to a user of an application, the user interface page comprising a first set of user interface controls,
in response to receiving a first interaction by the user, the first interaction being with a first user interface control of the first set of user interface controls, displaying to the user a second set of user interface controls, the second set of user interface controls comprising a dedicated user interface control usable by the user to modify an indicator associated with the first user interface control,
in response to receiving a second interaction by the user, the second interaction being with the dedicated user interface control, modifying the indicator, and
in response to receiving a third interaction by the user, the third interaction being with the modified indicator, displaying to the user, based on the modified indicator, a source of help that is specifically relevant to the first user interface control.

2. The method of claim 1 in which the modified indicator is initially hidden and in which the method comprises:
in response to receiving another interaction by the user with the first user interface control, displaying the modified indicator to the user.

3. The method of claim 2 in which the other interaction comprises the user hovering a display pointer over the first user interface control.

4. The method of claim 2 in which the other interaction with the first user interface control is different from the interaction with the first user interface control.

5. The method of claim 1 in which the source of help comprises an online source of help.

6. The method of claim 1 in which the modified indicator is part of a hidden tool tip.

7. The method of claim 1 in which the source of help comprises a webpage.

8. The method of claim 1 comprising:
displaying a second user interface page to a second user of the application, the second user interface page comprising a second user interface control usable by the second user to control whether or not the first user interface control is included in the first set of user interface controls, and
displaying to the second user, as part of the second user interface page, the modified indicator.

9. The method of claim 1 in which the modified indicator comprises a URL, IP address, or other link.

10. The method of claim 1 in which the application is associated with delivery of medical services.

11. The method of claim 1 in which the user is a physician.

12. The method of claim 1 comprising enabling another user of the application to modify the modified indicator.

13. The method of claim 1 in which the user has a permitted feature set that is a copy of a permitted feature set of another user, and in which the permitted feature set comprises the first set of user interface controls and the second set of user interface controls.

14. The method of claim 1 in which the interaction with the modified indicator comprises the user clicking on the modified indicator.

15. The method of claim 1 in which the first user interface control enables the user to specify a permitted feature set of the application for another user.

16. The method of claim 15 in which the permitted feature set comprises features that are displayed to the other user through user interface pages.

17. The method of claim 15 in which the permitted feature set comprises user interface controls.

18. The method of claim 15 in which the first user interface control enables the user to specify that the permitted feature set for the other user will be the same as a permitted feature set of a specified third user.

19. The method of claim 18 in which the third user is an origin user and the other user is a clone user.

20. The method of claim 15 in which the permitted feature set comprises features that are exposed to the other user as user interface presentation features.

21. The method of claim 15 in which the other user is affiliated with one or more institutions, and in which the permitted feature set depends on the institutions with which the other user is affiliated.

22. The method of claim 15 in which the permitted feature set comprises features associated with delivery of medical services.

23. The method of claim 1 in which the user interface page is served through a web browser.

24. The method of claim 1 in which the user is affiliated with an enterprise and is an authorized user of the application.

25. The method of claim 24 in which the user is an administrator of the enterprise.

26. The method of claim 1 in which the user is a medical practitioner, the method comprising
in response to receiving another interaction by the user with the first user interface control, displaying to the user information about a patient.

* * * * *